(12) United States Patent
Yamamura et al.

(10) Patent No.: US 6,346,603 B1
(45) Date of Patent: Feb. 12, 2002

(54) CRYSTAL OF DEPSIPEPTIDE DERIVATIVE AND PROCESS FOR PRODUCING THE SAME

(75) Inventors: Atsushi Yamamura, Osaka; Ryo Yamanishi, Tsukuba; Muneharu Ikushima, Osaka, all of (JP)

(73) Assignee: Fujisawa Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/530,591

(22) PCT Filed: Oct. 20, 1998

(86) PCT No.: PCT/JP98/04752

§ 371 Date: May 8, 2000

§ 102(e) Date: May 8, 2000

(87) PCT Pub. No.: WO99/24412

PCT Pub. Date: May 20, 1999

(30) Foreign Application Priority Data

Nov. 10, 1997 (JP) ............................. 9-307535

(51) Int. Cl.$^7$ ....................... C07D 273/00; C07K 11/02; A61K 38/15
(52) U.S. Cl. ........................................ 530/323; 514/11
(58) Field of Search ................. 530/317, 323; 514/9, 11, 18; 930/30

(56) References Cited

U.S. PATENT DOCUMENTS

| 5,514,773 A | 5/1996 | Nishiyama et al. ......... 530/317 |
| 5,646,244 A | 7/1997 | Nishiyama et al. ......... 530/317 |
| 5,856,436 A | 1/1999 | Nishiyama et al. ......... 530/317 |

| 6,235,875 B1 | * 5/2001 | Yamanishi et al. ......... 530/303 |

FOREIGN PATENT DOCUMENTS

| WO | 93/01953 | * 2/1993 |
| WO | 93/19053 | * 9/1993 |
| WO | 94/19334 | * 9/1994 |
| WO | 97/02256 | * 1/1997 |

* cited by examiner

Primary Examiner—Jeffrey E. Russel
(74) Attorney, Agent, or Firm—Oblon, Spivak, McClelland, Maier & Neustadt, P.C.

(57) ABSTRACT

Crystals of a depsipeptide derivative of formula (IV):

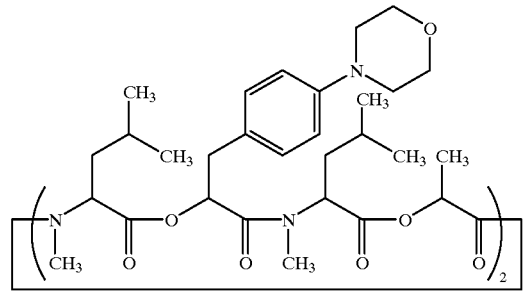

having an antiparasitic activity and methods for producing such crystals. Such crystals include crystals (I), (II) and (III) that have particular physicochemical properties or characteristics, such as excellent filtration properties during crystallization, great fluidity, good specific volume. As a consequence, such crystals have improved handling ability during production resulting in enhanced production efficiency and increased crystal yield. Methods are also provided for producing such crystals.

12 Claims, 12 Drawing Sheets

CRYSTAL OF DEPSIPEPTIDE DERIVATIVE AND PROCESS FOR PRODUCING THE SAME

TECHNICAL FIELD

The present invention relates to novel crystals of depsipeptide derivative (IV) with an antiparasitic activity, and a method for producing the same.

BACKGROUND ART

The depsipeptide derivative (IV) represented by the following formula has been known as a compound with an excellent antiparasitic activity to animals and human beings, and WO 93/19053 and WO 97/02256 disclose a method for producing the same.

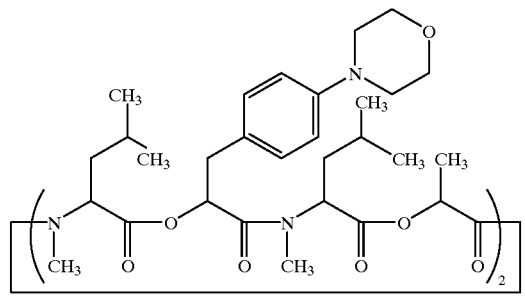

The former WO 93/19053 specifically discloses a method for producing amorphous depsipeptide derivative (IV) by way of the following processes (nine processes in total).

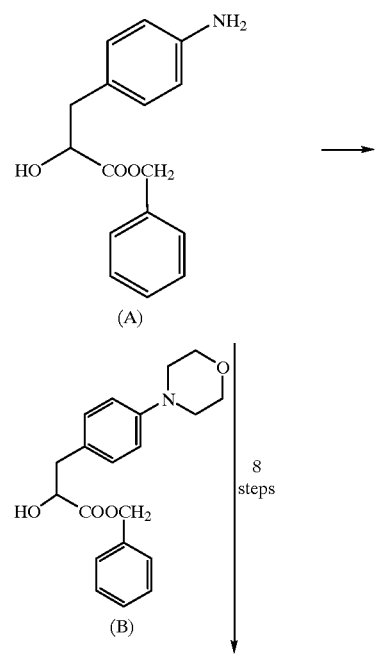

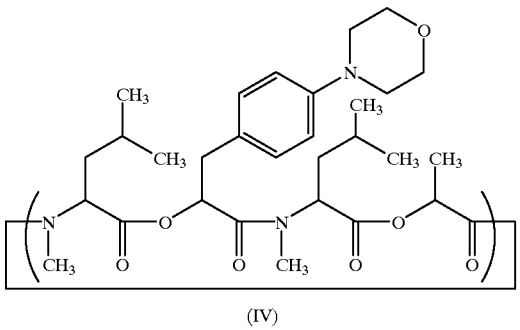

(IV)

According to the method, however, all the intermediate products produced during the course by way of the compound (B) to the objective compound (IV) have basic morpholino groups within the molecules and therefore, they should be handled with precise caution and they are purified by re-crystallization with much difficulty. Because the resulting objective compound (IV) itself is poor in terms of crystallinity, the compound has a variety of disadvantages in terms of production efficiency and handle-ability such that the compound requires purification by column chromatography and the like. Hence, it cannot be said that the method is suitable for industrial scale.

So as to overcome such problems, thus, the method of the latter WO 97/02256 is proposed. According to the method, a depsipeptide derivative in crystal can be recovered, but the subsequent research works indicate that the crystal is poor in respect of filtration properties during crystallization and of fluidity and specific volume [referring the volume occupied by a unit mass (1 g), which is equal to the reciprocal of the density].

DISCLOSURE OF INVENTION

With attention focused on the aforementioned circumstance, the present invention has been attained, and the purpose of the present invention is to provide novel crystals of depsipeptide derivative with excellent filtration properties during crystallization, great fluidity, good specific volume and the like, thereby as a consequence of the improvement in the handle-ability during production, resulting in an enhanced production efficiency and an increased yield of the crystal, and to provide a method for producing such crystals at a high efficiency.

The crystals (I), (II) and (III) of the depsipeptide derivative (IV) according to the present invention capable of overcoming the problems described above, individually have the following physico-chemical properties.

Crystal (I): substantially having the powdery X-ray diffraction characteristic properties described in Table 1 and having an endothermic peak substantially at 155° C. by differential thermal analysis.

TABLE 1

| 2θ value (°) | Relative intensity (%) | 2θ value (°) | Relative intensity (%) | 2θ value (°) | Relative intensity (%) | 2θ value (°) | Relative intensity (%) |
|---|---|---|---|---|---|---|---|
| 5.67 | 100.0 | 13.15 | 19.52 | 19.86 | 15.18 | 26.48 | 2.33 |
| 6.46 | 0.41 | 14.56 | 8.83 | 20.19 | 10.19 | 26.93 | 1.22 |
| 7.36 | 1.01 | 15.01 | 42.59 | 20.47 | 6.81 | 27.66 | 5.24 |

TABLE 1-continued

| 2θ value (°) | Relative intensity (%) | 2θ value (°) | Relative intensity (%) | 2θ value (°) | Relative intensity (%) | 2θ value (°) | Relative intensity (%) |
|---|---|---|---|---|---|---|---|
| 7.92 | 3.12 | 15.44 | 61.33 | 20.84 | 7.03 | 28.03 | 4.70 |
| 8.74 | 5.339 | 15.97 | 26.84 | 21.62 | 8.83 | 28.60 | 2.65 |
| 9.34 | 9.94 | 16.80 | 16.13 | 22.15 | 6.71 | 29.45 | 1.26 |
| 10.35 | 10.32 | 17.07 | 10.84 | 22.52 | 7.35 | 29.77 | 1.60 |
| 11.27 | 29.39 | 17.55 | 2.39 | 23.04 | 1.55 | 30.61 | 1.05 |
| 11.39 | 25.81 | 18.33 | 19.34 | 23.75 | 5.81 | 31.94 | 1.36 |
| 11.88 | 5.52 | 18.96 | 7.79 | 25.05 | 4.03 | | |
| 12.69 | 5.24 | 19.42 | 3.87 | 26.07 | 1.40 | | |

Crystal (II): substantially exerting the powdery X-ray diffraction characteristic properties described in Table 2 and having an endothermic peak substantially at 182° C. by differential thermal analysis.

TABLE 2

| 2θ value (°) | Relative intensity (%) | 2θ value (°) | Relative intensity (%) | 2θ value (°) | Relative intensity (%) | 2θ value (°) | Relative intensity (%) |
|---|---|---|---|---|---|---|---|
| 4.79 | 35.86 | 13.56 | 47.83 | 19.10 | 47.83 | 25.00 | 6.48 |
| 4.89 | 35.50 | 14.20 | 32.70 | 19.51 | 32.02 | 25.36 | 6.63 |
| 5.58 | 14.69 | 14.64 | 30.02 | 19.91 | 17.57 | 26.06 | 4.65 |
| 7.00 | 1.16 | 15.75 | 41.82 | 21.39 | 23.82 | 27.31 | 8.61 |
| 9.09 | 8.79 | 15.56 | 52.50 | 22.02 | 13.34 | 27.95 | 8.61 |
| 9.69 | 5.45 | 16.26 | 66.32 | 22.54 | 14.01 | 29.06 | 6.48 |
| 10.52 | 100.0 | 16.63 | 40.67 | 22.84 | 16.58 | 29.60 | 3.12 |
| 10.85 | 31.10 | 17.07 | 40.29 | 23.16 | 17.32 | 30.38 | 3.79 |
| 11.49 | 7.10 | 18.34 | 32.70 | 23.82 | 26.21 | 31.75 | 2.07 |
| 12.40 | 11.86 | 18.73 | 24.40 | 24.44 | 9.51 | | |

Crystal (III): substantially exerting the powdery X-ray diffraction characteristic properties described in Table 3 and having an endothermic peak substantially at 194° C. by differential thermal analysis.

TABLE 3

| 2θ value (°) | Relative intensity (%) | 2θ value (°) | Relative intensity (%) | 2θ value (°) | Relative intensity (%) | 2θ value (°) | Relative intensity (%) |
|---|---|---|---|---|---|---|---|
| 6.02 | 100.0 | 12.17 | 30.53 | 19.04 | 14.75 | 26.07 | 3.83 |
| 6.20 | 87.04 | 13.20 | 5.81 | 19.44 | 7.78 | 26.73 | 2.78 |
| 6.30 | 50.17 | 14.45 | 16.17 | 19.98 | 10.99 | 28.19 | 2.66 |
| 6.82 | 2.60 | 15.19 | 19.22 | 21.21 | 11.72 | 29.13 | 1.61 |
| 8.08 | 1.22 | 16.10 | 19.22 | 21.99 | 17.36 | 30.05 | 1.22 |
| 9.45 | 2.32 | 16.70 | 26.47 | 22.16 | 11.97 | 30.61 | 1.26 |
| 9.64 | 1.90 | 16.87 | 24.10 | 22.88 | 8.40 | 31.27 | 0.76 |
| 10.48 | 2.10 | 17.74 | 6.62 | 22.99 | 9.94 | | |
| 12.03 | 20.51 | 18.45 | 7.38 | 24.26 | 10.52 | | |

The methods for producing the crystals (I), (II) and (III) of the depsipeptide derivative (IV) according to the present invention, having overcome the problems, are individually as follows.

Crystal (I)

The following method (1) or (2) may essentially be used.
(1) The depsipeptide derivative (IV) is added to acetone and dissolved therein, followed by further addition of water for crystallization, or
(2) the depsipeptide derivative (IV) is added to tetrahydrofuran, acetonitrile or acetone and dissolved, followed by addition of isopropyl ether for crystallization.

Crystal (II)

The crystal (I) is added to ethanol and dissolved therein, followed by addition of isopropyl ether for crystallization.

Crystal (III)

The crystal (II) is added to ethyl acetate and dissolved therein, followed by further addition of isopropyl ether for crystallization.

BEST MODE FOR CARRYING OUT THE INVENTION

The present inventors have examined the filtration properties during crystallization, the specific volume and fluidity (adhesion properties) with respect to the crystal of the depsipeptide derivative (IV) as recovered by the method described in WO 97/02256. Consequently, the inventors have found that the crystal of the depsipeptide derivative (IV) recovered by the above publication (sometimes referred to as "prior art crystal" for convenience) has problems that poor filtration properties during crystallization and a large specific volume result in a longer production time; additionally distinguished adhesion properties and poor fluidity result in the loss of the yield due to the adhesion thereof, and the like.

So as to improve such various disadvantages during production, the inventors have made intensive investigations. Consequently, the inventors have found that the novel crystals [(I), (II) and (III)] of the depsipeptide derivative (IV) with the distinguished improvement in above disadvantages can be recovered, by dissolving the prior art crystal in a specific solvent for crystallization. Thus, the present invention has been attained.

The derivative (IV) described in aftermentioned Example shows stereostructural formula of the above depsipeptide derivative (IV), the both derivatives are identical.

The novel crystal (I) of the depsipeptide derivative (IV) in accordance with the present invention is firstly described.

Figure 1:
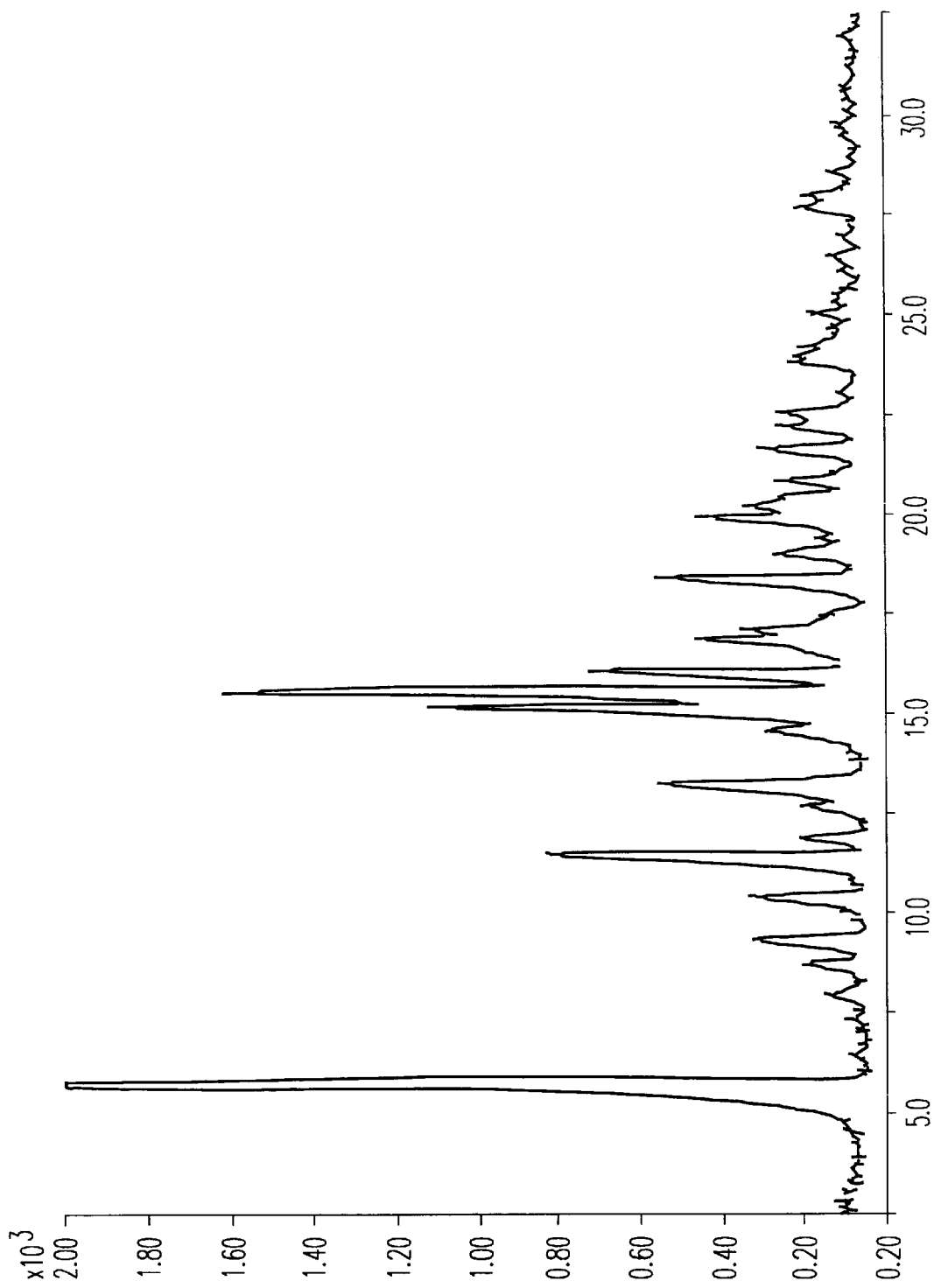
FIG. 1 is a chart of the powdery X-ray diffraction pattern of the crystal (I) of the present invention.

The crystal (I) substantially has the powdery X-ray diffraction characteristic properties described in Table 1. Herein, the powdery X-ray diffraction was conducted under conditions of X-ray monochromated CuK α radiation by using a powdery X-ray diffractometer MPD1880 manufactured by Philip Co., and FIG. 1 shows the resulting analysis pattern. The analysis data of FIG. 1 are arranged in the increasing order of the 2θ value, together with the relative intensity (%) corresponding to the 2θ value, which are collectively shown in Table 1. The crystal (I) in accordance with the present invention may satisfy the characteristic pattern shown in Table 1 above, with no requirement of any strict identity. Furthermore, the crystal (I) is required to have an endothermic peak substantially at 155° C. by differential thermal analysis (DTA). The differential thermal analysis was conducted under the following analysis conditions in nitrogen stream at a increasing temperature speed of 10° C./min, by using a thermal analyzer TG/DTA manufactured by Seiko Instruments Inc.;

Reference: α-alumina,

Cell: open.

Figure 2:
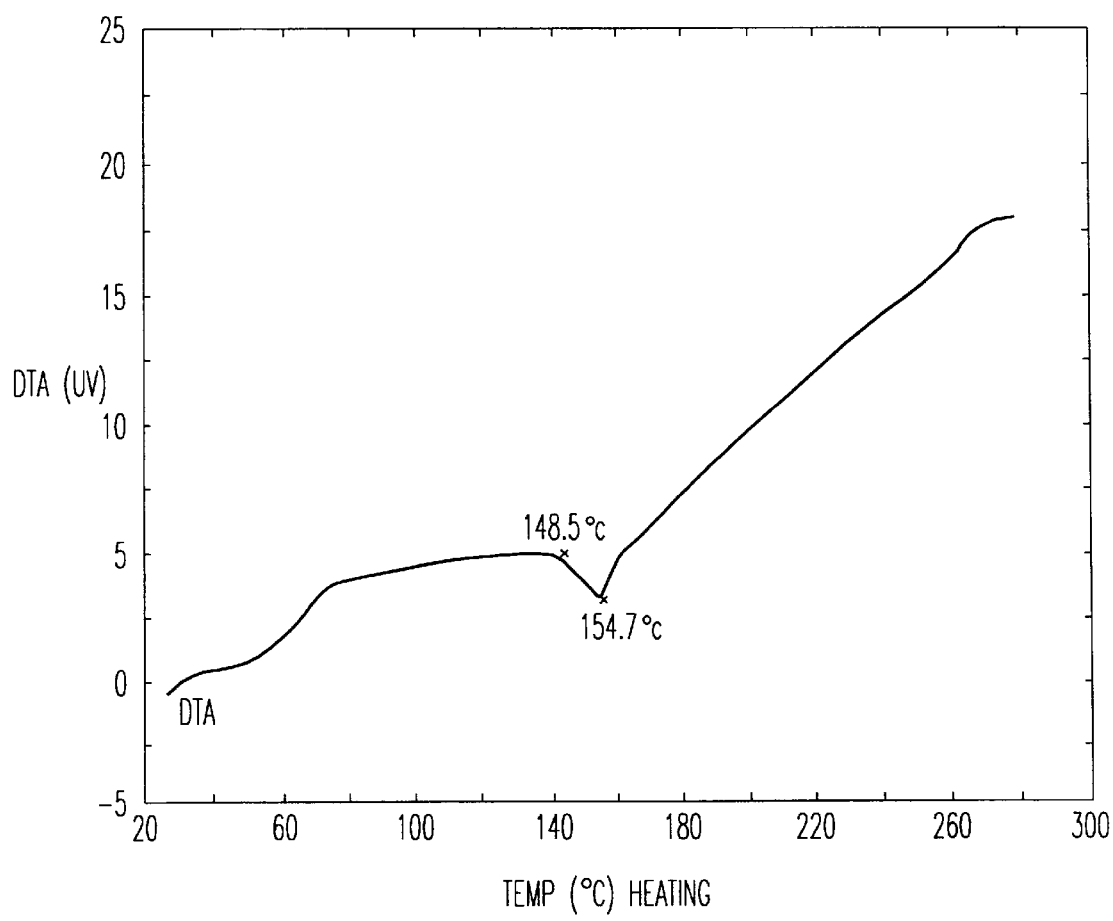
FIG. 2 is a chart of the differential thermal analysis of the crystal (I) of the present invention.

FIG. 2 shows the resulting analysis pattern. All of the crystals with an endothermic peak substantially at 155° C. by differential thermal analysis are encompassed within the scope of the crystal (I) of the present invention.

Figure 3:
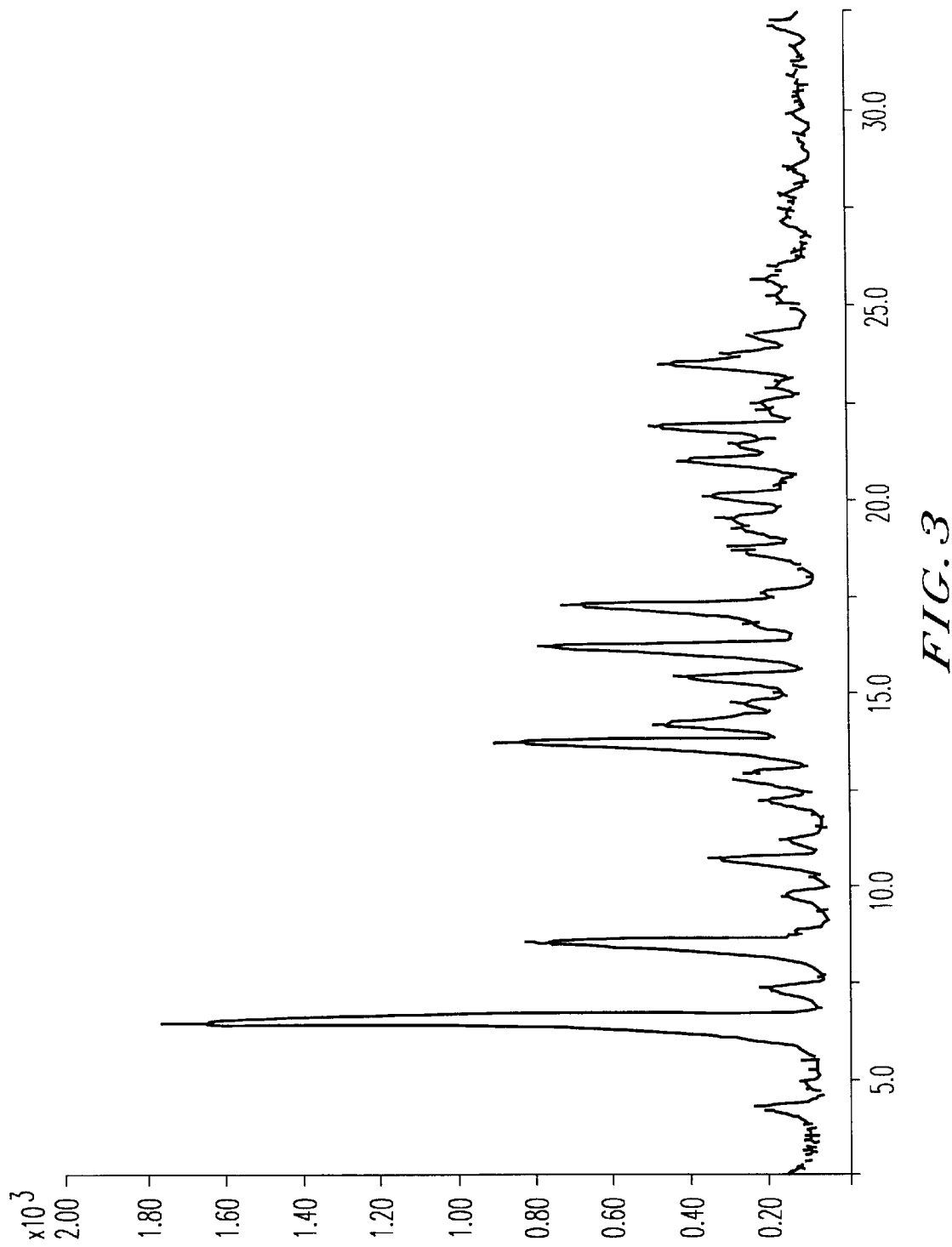
FIG. 3 is a chart of the powdery X-ray diffraction pattern of the prior art crystal.
Figure 4:
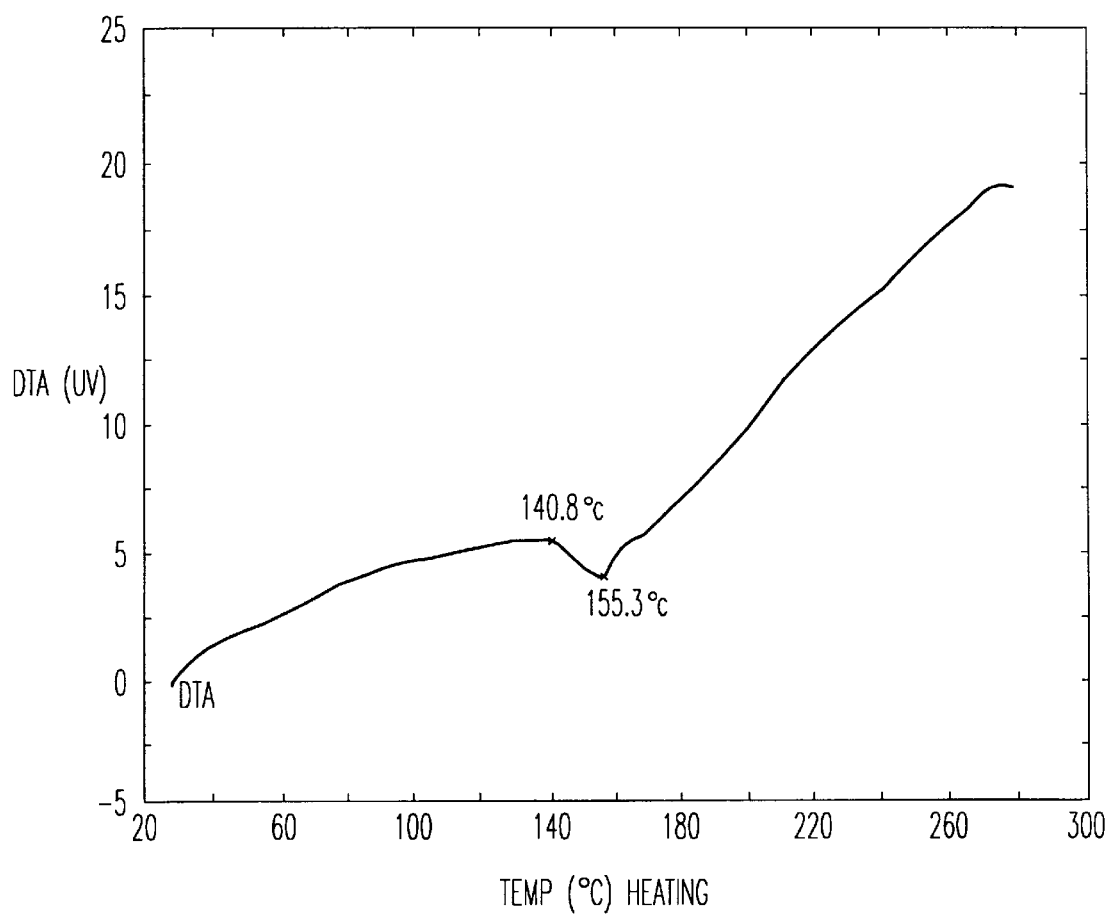
FIG. 4 is a chart of the differential thermal analysis of the prior art crystal.

Based on the two types of physico-chemical properties described above, the crystal (I) of the present invention can distinctively be discriminated from the prior art crystal recovered by the method described in the WO 97/02256. For comparison, the powdery X-ray diffraction pattern of the prior art crystal is shown in FIG. 3; and the differential thermal analysis pattern thereof is shown in FIG. 4. The endothermic peak then by differential thermal analysis is substantially at 155° C. Additionally, the analysis data of FIG. 3 are arranged in the increasing order of the 2θ value, together with the relative intensity (%) corresponding to the 2θ value, which are collectively shown in Table 4.

TABLE 4

| 2θ value (°) | Relative intensity (%) | 2θ value (°) | Relative intensity (%) | 2θ value (°) | Relative intensity (%) | 2θ value (°) | Relative intensity (%) |
|---|---|---|---|---|---|---|---|
| 4.30 | 7.48 | 12.94 | 10.34 | 20.45 | 16.82 | 26.01 | 4.63 |
| 4.89 | 0.93 | 13.62 | 52.42 | 20.95 | 20.77 | 27.11 | 4.00 |
| 6.49 | 100.0 | 14.08 | 24.87 | 21.36 | 11.68 | 27.85 | 3.05 |
| 7.34 | 7.48 | 14.71 | 11.17 | 21.74 | 23.14 | 28.51 | 2.23 |
| 8.41 | 48.38 | 15.30 | 20.08 | 21.85 | 25.38 | 29.27 | 0.66 |
| 8.54 | 36.61 | 16.07 | 44.00 | 22.51 | 7.61 | 29.89 | 2.38 |
| 8.84 | 3.70 | 16.65 | 9.54 | 22.90 | 5.54 | 30.87 | 2.01 |
| 9.76 | 5.42 | 17.15 | 39.74 | 23.42 | 23.38 | 31.59 | 1.73 |
| 10.67 | 18.09 | 17.59 | 7.61 | 23.73 | 13.11 | 32.14 | 5.42 |
| 11.20 | 6.93 | 18.73 | 11.85 | 24.21 | 9.23 | | |
| 12.20 | 8.48 | 19.13 | 10.01 | 25.14 | 4.42 | | |
| 12.69 | 12.03 | 19.48 | 13.48 | 25.62 | 6.68 | | |

Figure 5:
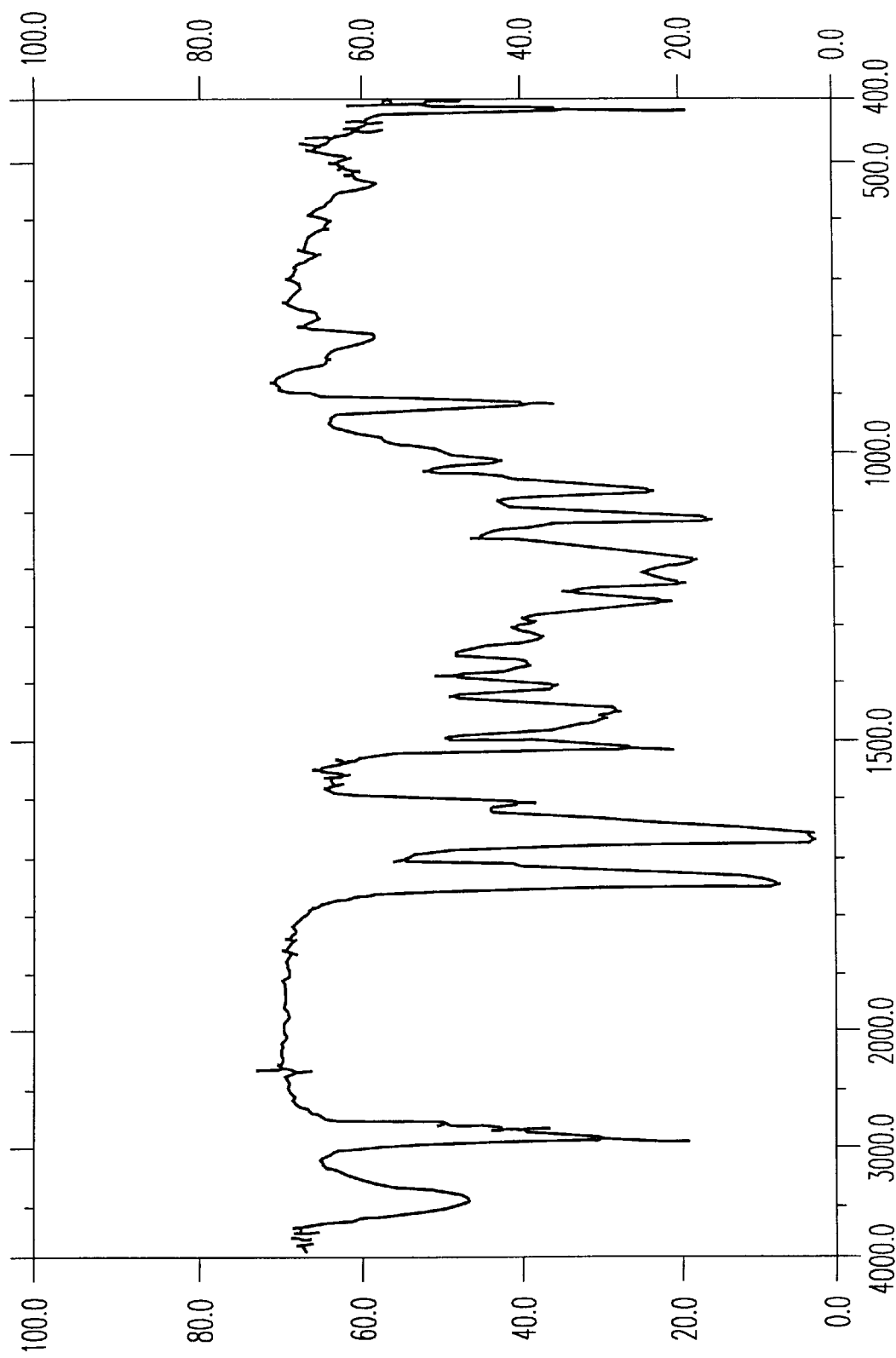
FIG. 5 is an IR chart of the crystal (I) of the present invention.

The crystal (I) of the present invention is characterized by the powdery X-ray diffraction characteristic properties and the endothermic peak of differential thermal analysis. As another physico-chemical property, the IR spectral data (KBr) is shown in FIG. 5 and additionally its absorption value shows in Table 5. Table 5 further shows the IR absorption value of the crystal (II) and (III) in accordance with the present invention, together with the IR absorption value of the prior art crystal.

TABLE 5

| Crystal (I) (cm$^{-1}$) | Crystal (II) (cm$^{-1}$) | Crystal (III) (cm$^{-1}$) | Prior art Crystal (V) (cm$^{-1}$) |
|---|---|---|---|
| 3510 | 3460 | 3480 | 3510 |
| 2965 | 2965 | 2965 | 2960 |
| 2875 | 2875 | 2875 | 2875 |
| 2830 | 2825 | | |
| 1746 | 1749 | 1742 | 1745 |
| | | 1737 | 1720 |
| 1670 | 1670 | | |
| 1665 | | 1666 | 1664 |
| 1656 | | 1657 | 1656 |
| 1626 | 1616 | 1631 | 1618 |
| 1519 | 1518 | 1519 | 1518 |
| | 1482 | 1490 | |
| | | 1484 | |
| 1472 | 1471 | 1475 | 1474 |
| 1468 | 1466 | 1467 | 1467 |
| 1458 | 1456 | 1459 | 1459 |
| 1451 | 1451 | | 1451 |
| | | 1420 | 1420 |
| 1414 | 1415 | 1415 | 1414 |
| 1378 | 1386 | 1380 | 1377 |
| 1372 | | 1378 | 1371 |
| | | | 1341 |
| 1332 | 1329 | 1330 | 1330 |
| 1327 | | | |
| 1303 | 1302 | 1302 | 1302 |
| 1265 | 1263 | 1264 | 1264 |
| 1232 | 1231 | 1234 | 1233 |
| 1192 | 1190 | 1191 | 1191 |
| 1123 | 1123 | 1123 | 1122 |
| 1075 | 1076 | 1077 | 1077 |
| 1027 | 1027 | 1027 | 1027 |
| 928 | 928 | 930 | 929 |
| 421 | 425 | 425 | 421 |
| 412 | 416 | 421 | |

Figure 6:
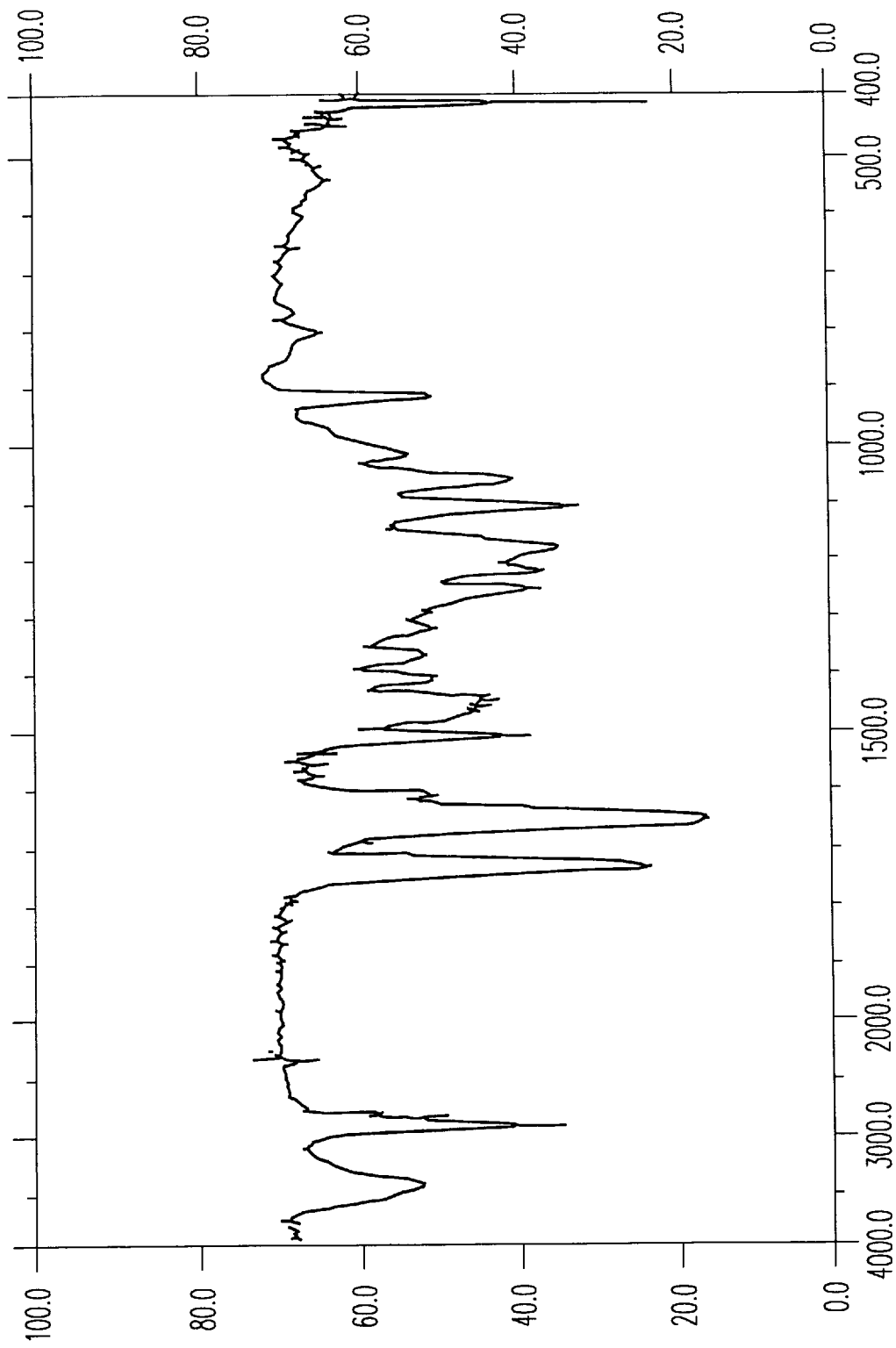
FIG. 6 is an IR chart of the prior art crystal.

For reference furthermore, the analysis pattern of the IR spectrum (KBr) of the prior art crystal is also shown in FIG. 6.

Then, the crystal (II) of the present invention is now described below.

Figure 7:
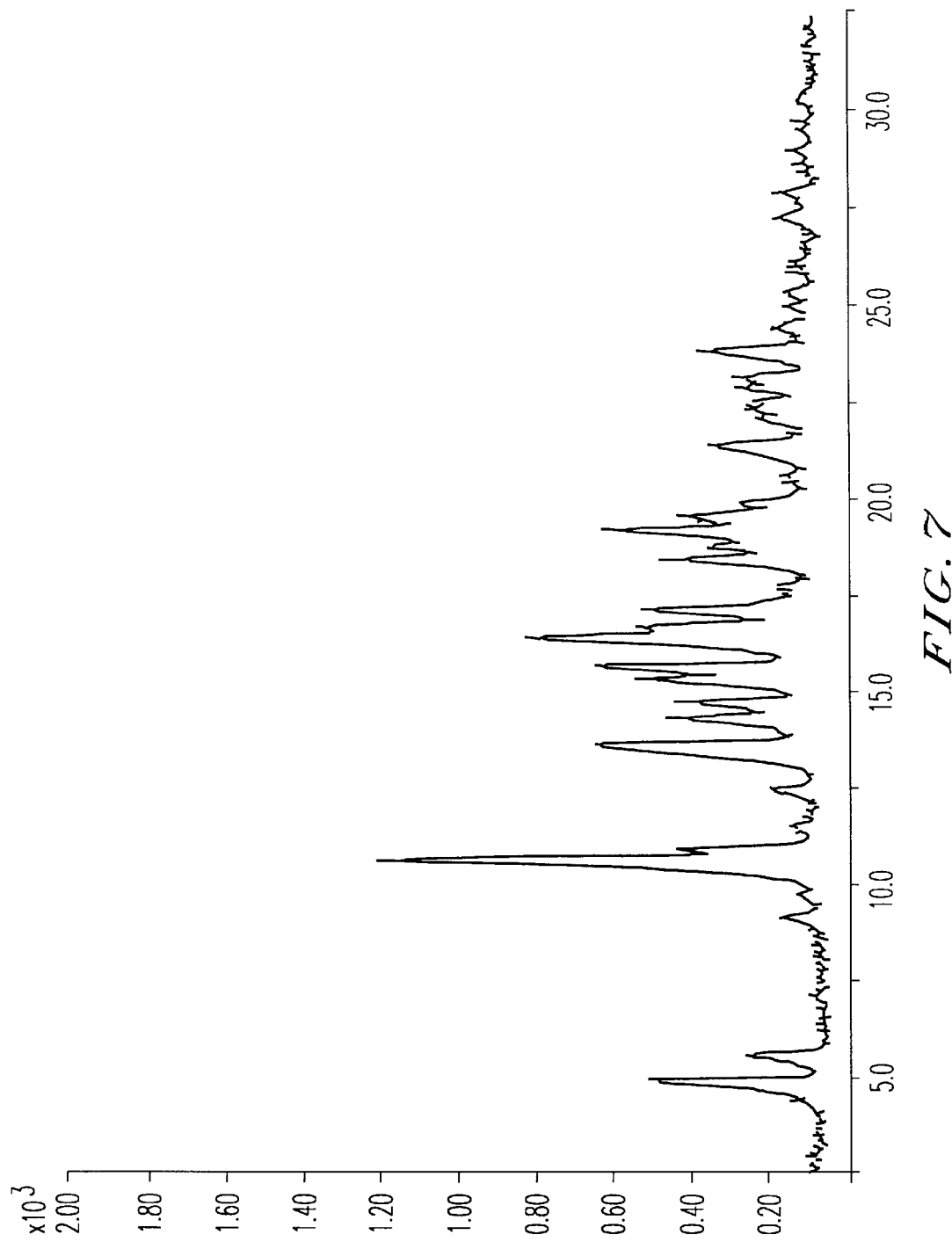
FIG. 7 is a chart of the powdery X-ray diffraction pattern of the crystal (II) of the present invention.

The crystal (II) substantially has the powdery X-ray diffraction characteristic properties described in Table 2, and the resulting analysis pattern is shown in FIG. 7. Additionally, the analysis data of FIG. 7 are arranged in the increasing order of the 2θ values, together with the relative intensity (%) corresponding to the 2θ value, which are collectively shown in Table 2. The crystal (II) of the present invention may substantially satisfy the characteristic pattern shown in Table 2 above, with no requirement of any strict identity.

Figure 8:
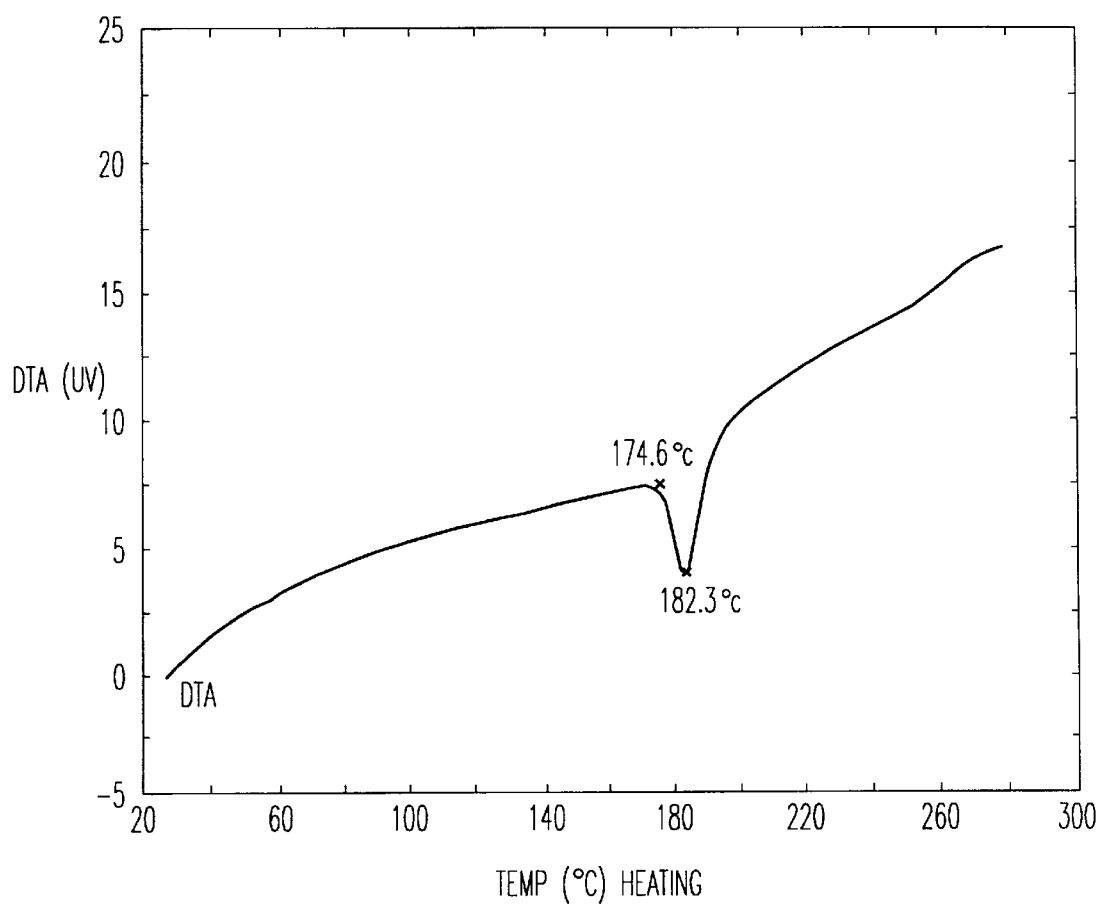
FIG. 8 is a chart of the differential thermal analysis of the crystal (II) of the present invention.

The crystal (II) furthermore is required to have an endothermic peak substantially at 182° C. FIG. 8 shows the resulting analysis pattern. All of the crystals having an endothermic peak substantially at 182° C. by differential thermal analysis are encompassed within the scope of the crystal (II) of the present invention.

Figure 9:
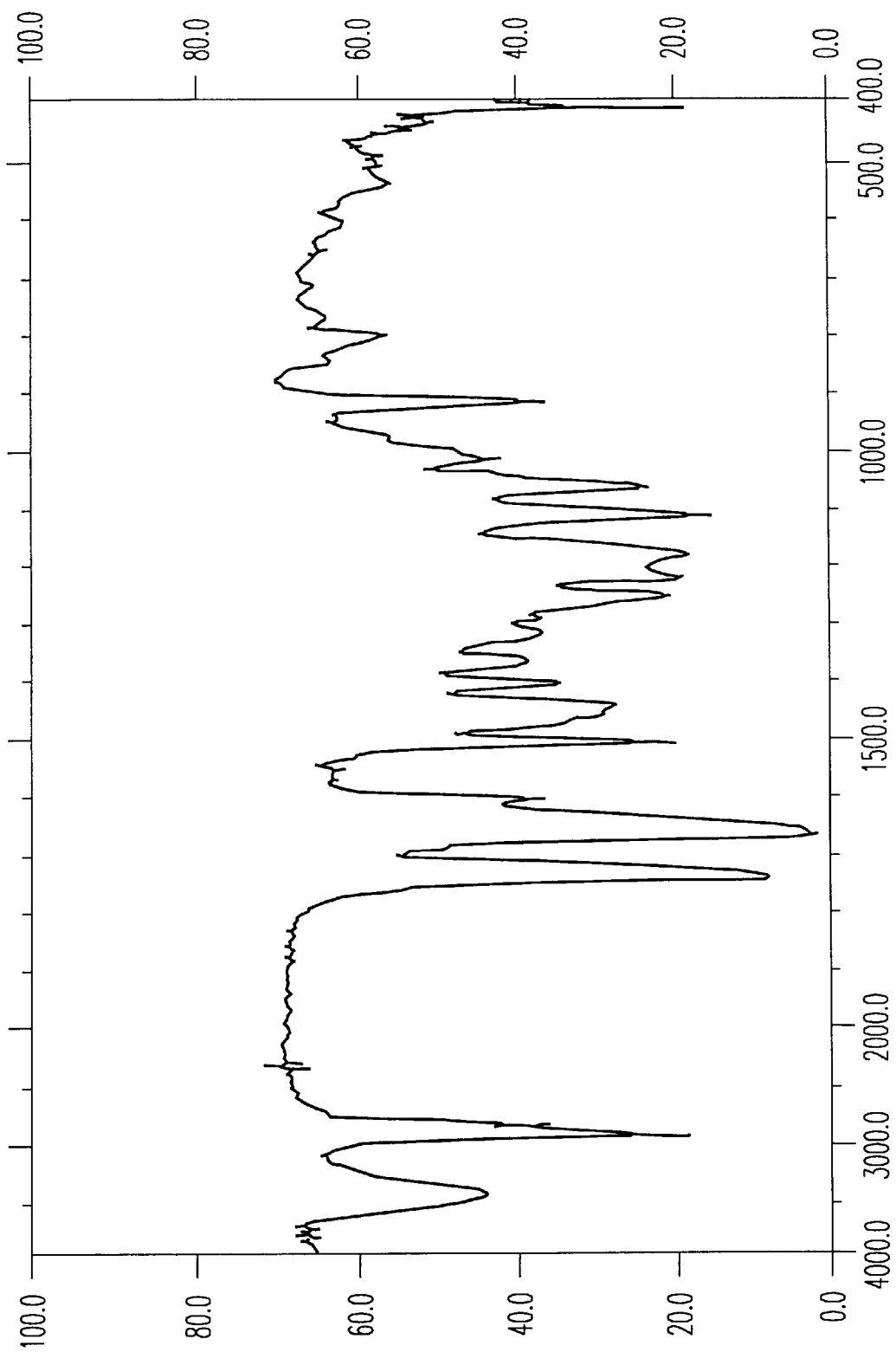
FIG. 9 is an IR chart of the crystal (II) of the present invention.

Based on the two types of physico-chemical properties described above, the crystal (II) of the present invention can distinctively be discriminated from the prior art crystal recovered by the method described in WO 97/02256. The results of the IR spectral analysis (KBr) as another physico-chemical property are shown in FIG. 9.

Finally, the crystal (III) of the present invention is now described.

Figure 10:
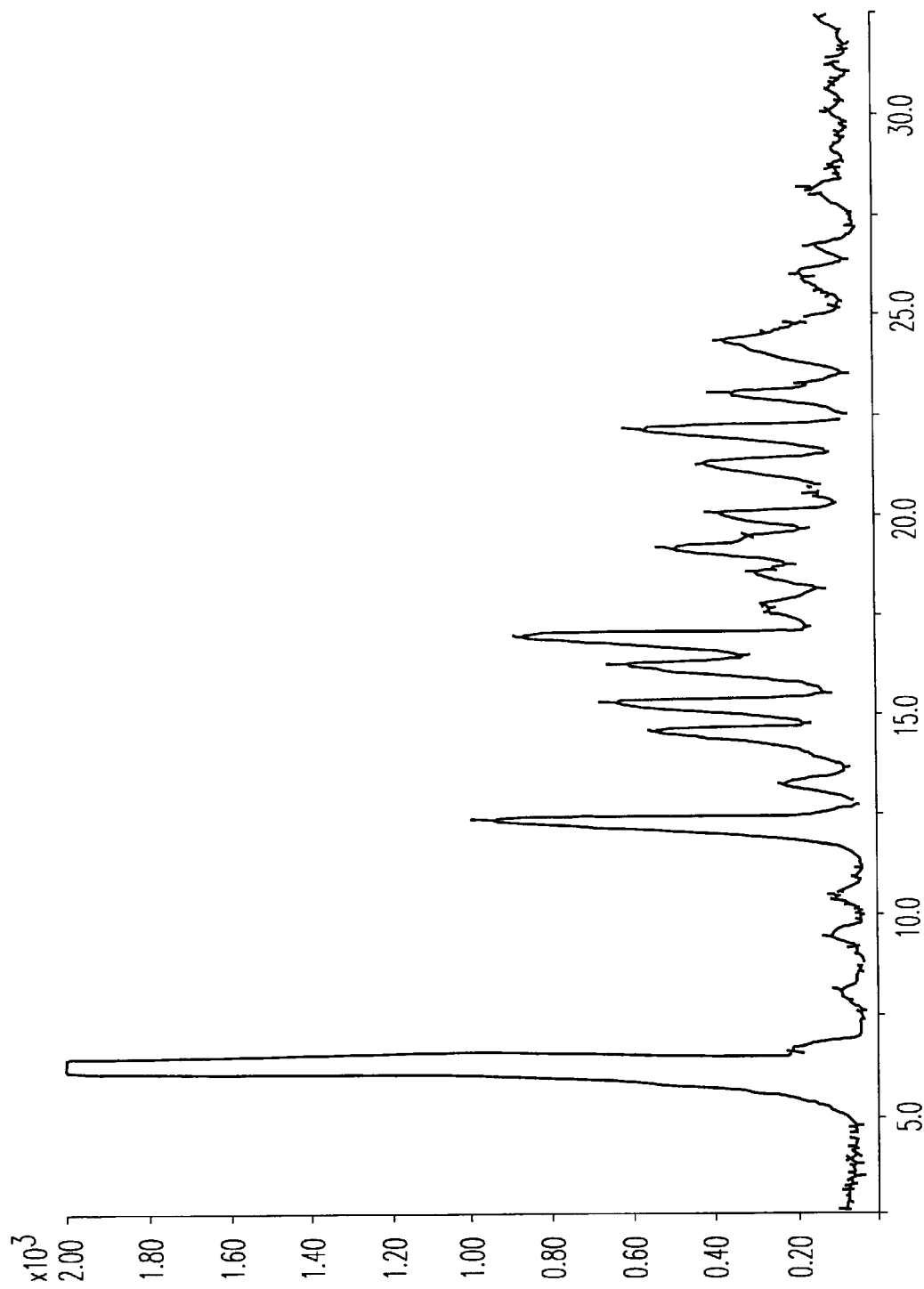
FIG. 10 is a chart of the powdery X-ray diffraction pattern of the crystal (III) of the present invention.

The crystal (III) substantially has the powdery X-ray diffraction characteristic properties described in Table 3, and FIG. 10 shows the resulting analysis pattern. Additionally, the analysis data of FIG. 10 are arranged in the increasing order of the 2θ value, together with the relative intensity (%) corresponding to the 2θ value, which are collectively shown in Table 3. The crystal (II) of the present invention may substantially satisfy the characteristic pattern shown in Table 3, with no requirement of any strict identity.

Figure 11:
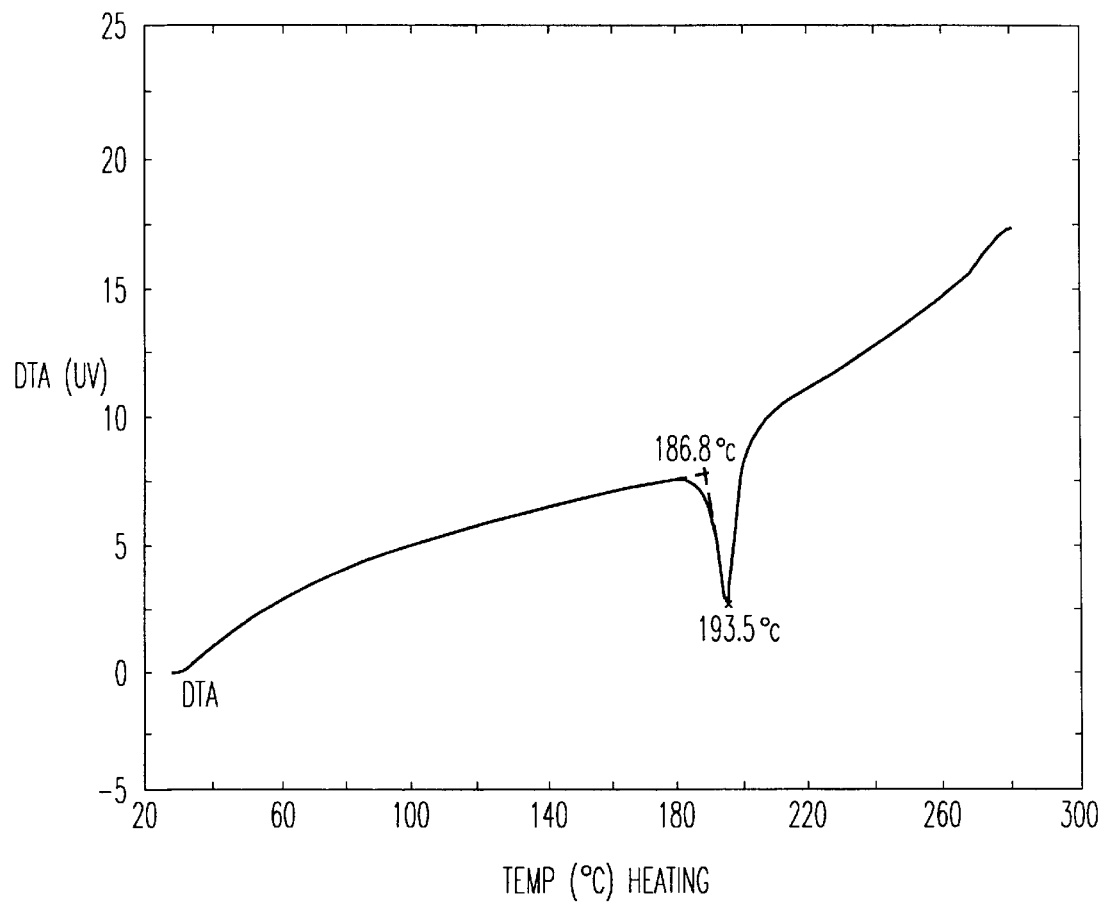
FIG. 11 is a chart of the differential thermal analysis of the crystal (III) of the present invention.

Furthermore, the crystal (III) is required to have an endothermic peak substantially at 194° C. by differential thermal analysis. FIG. 11 shows the resulting analysis pattern. All of the crystals with an endothermic peak substantially at 194° C., are encompassed within the scope of the crystal (III) of the present invention.

Figure 12:
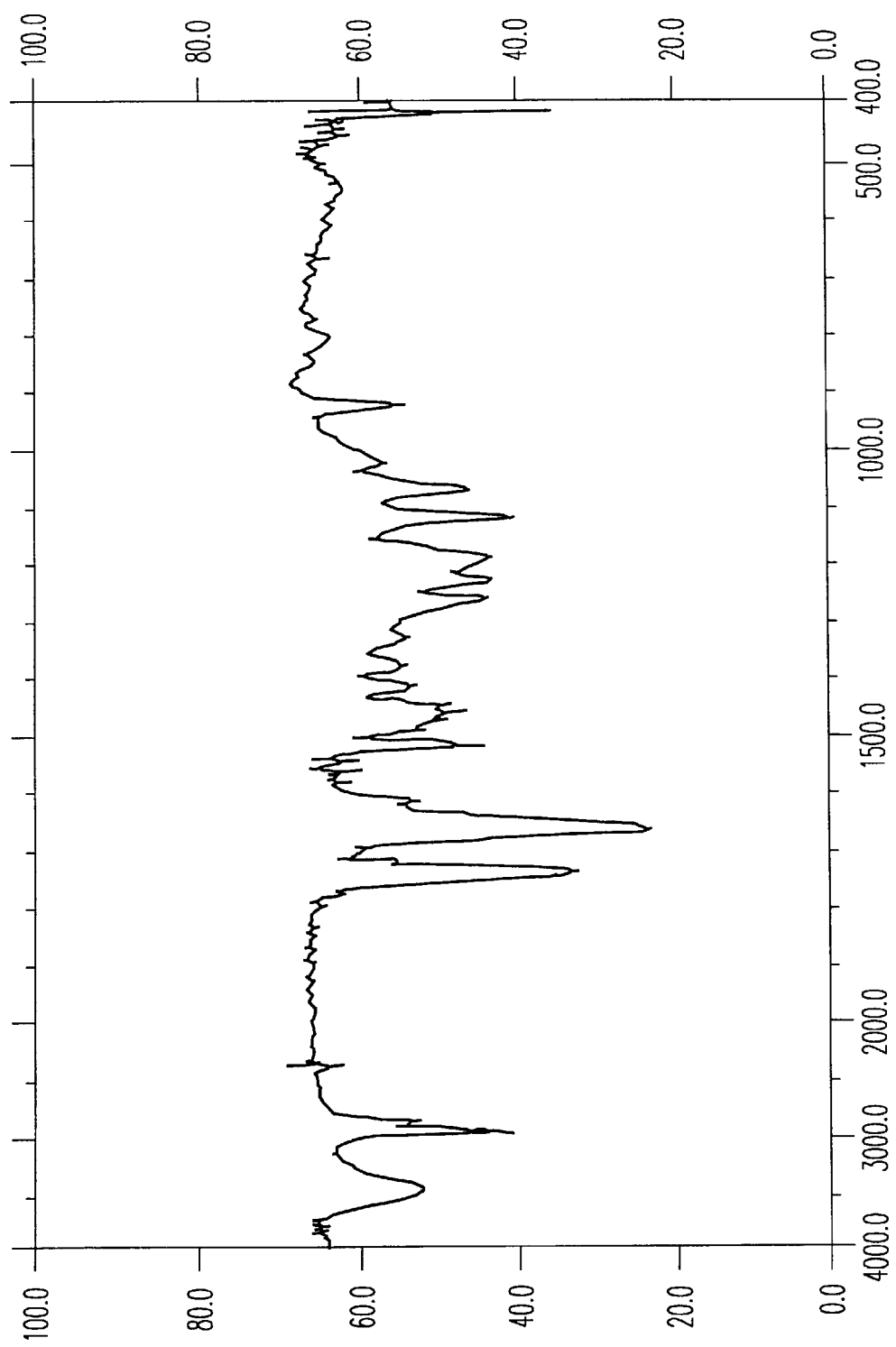
FIG. 12 is an IR chart of the crystal (III) of the present invention.

Based on the two types of the physico-chemical properties, the crystal (III) of the present invention can distinctively be discriminated from the prior art crystal recovered by the method described in WO 97/02256, and as another physico-chemical property, the IR spectrum (KBr) was analyzed and the results are shown in FIG. 12.

Following is descriptions regarding methods for producing the novel crystals (I), (II) and (III) in accordance with the present invention.

Firstly, the crystal (I) can be produced by the above methods (1) and (2).

Specifically, the method (1) is one comprising adding the depsipeptide derivative (IV) to acetone to dissolve the derivative therein and further adding water to the resulting mixture for crystallization; and the method (2) comprises adding the depsipeptide derivative (IV) to tetrahydrofuran, acetonitrile or acetone to dissolve the derivative therein and adding isopropyl ether to the resulting mixture for crystallization.

For comparing the two methods, these methods are different in that the method (2) comprises crystallization by the addition of isopropyl ether while the method (1) comprises crystallization by the addition of water. According to the method (1), furthermore, the addition of seed crystal is substantially never required, while the method (2) comprises substantial addition of seed crystal.

By any of the methods, however, the temperature for dissolving the prior art crystal and the crystallization temperature thereof and the like are not specifically limited, and generally, these procedures are generally conducted under cooling, at ambient temperature or under heating. The prior art crystal per se can be obtained by the Example 5 described in WO 97/02256 and the like.

Then, the crystal (II) can be recovered by adding the crystal (I) recovered by the method (1) or (2) to ethanol to dissolve the crystal (1) therein and subsequently adding isopropyl ether to the resulting mixture for crystallization. The temperature for dissolution and the crystallization temperature and the like are not specifically limited, and these procedures are generally conducted under cooling, at ambient temperature and under heating.

Furthermore, the crystal (III) can be recovered by adding the crystal (II) recovered by the method described above to ethyl acetate to dissolve the crystal therein and further adding isopropyl ether to the resulting mixture for crystallization. The temperature for dissolution and the crystallization temperature are not specifically limited, and these procedures are generally conducted under cooling, at ambient temperature and under heating.

The present invention is now described in detail based on the following examples. The following examples are in no way intended to limit the present invention, and without departing from the spirit of the present invention, modifications thereof are all encompassed within the technical scope of the present invention.

The formal names of the abbreviations used in the following description are as follows.

Me: methyl

Leu: leucine p-MorPhLac:2-hydroxy-3-(4-morpholinophenyl) propionic-acid[β-(p-morpholinophenyl)lactic acid]

Lac: 2-hydroxypropionic acid [lactic acid]

D: D type

EXAMPLE 1

Production of Crystal (I) (No.1)

Sodium hydrogencarbonate (0.27 g) and bis(2-oxo-3-oxazolidinyl)phosphine chloride (0.13 g) were added to a solution of 3HCl.H-MeLeu-D-p-MorPhLac-MeLeu-D-Lac-MeLeu-D-p-MorPhLac-MeLeu-D-Lac-OH (0.404 g) in methylene chloride (162 ml), and the resulting mixture was stirred for 71 hours. The solvent was removed under reduced pressure, followed by addition of water (50 ml) to extract the resulting product three times (50 ml×3) in ethyl acetate. The resulting ethyl acetate layer was washed with saturated saline and dried over anhydrous sodium sulfate, and the solvent was removed under reduced pressure. The resulting crude product was purified by silica gel column chromatography, was eluted with a mixture solution of hexane, ethyl acetate and ethanol [50:45:5(v/v)]. The solvent in the eluted fractions containing the desired product was removed under reduced pressure to recover amorphous depsipeptide derivative (IV).

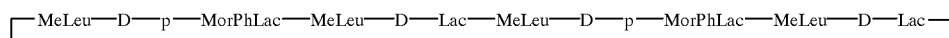

The method was conducted in a similar manner to that of the Example 5 described in WO 93/19053.

The amorphous depsipeptide derivative (IV) (2.00 g) thus recovered was charged to a 100 ml three-necked flask, followed by addition of 20 ml of methanol to dissolve the derivative at ambient temperature (24° C.). By dropwise adding water (40 ml) to the resulting solution over about 30 minutes, the depsipeptide derivative (IV) in crystal was deposited. After stirring further at ambient temperature for 2 hours, the deposited crystal was filtered off and washed with water (10 ml). The resulting crystal was dried at 40° C. for 6 hours to recover the depsipeptide derivative (IV) in crystal (1.90 g). The crystal of the depsipeptide derivative (IV), thus recovered, corresponds to the "prior art crystal" described above. So as to discriminate the crystal from other crystals, for convenience, the crystal is referred to as crystal (V).

The crystal (2.0 g) was then charged to a 100 ml three-necked flask, followed by addition of acetone (20 ml) to dissolve the crystal at ambient temperature (25° C.). By dropwise adding water (20 ml) to the solution over about 30 minutes, a crystal was deposited. After stirring further for 2 hours at ambient temperature, the deposited crystal was filtered off and washed with a mixture solution (5 ml) of acetone and water (1:2). The resulting crystal was dried at 40° C. for 5 hours under reduced pressure to recover the crystal (I) (1.90 g) of the depsipeptide derivative (IV).

EXAMPLE 2

Production of Crystal (I) (No.2)

The crystal (II) of the depsipeptide derivative (IV) was produced in the same manner as in Example 5 described below. Then, the crystal (II) (1.5 g) was charged to a 50 ml three-necked flask, followed by addition of 3 ml of tetrahydrofuran to dissolve the crystal at ambient temperature (25° C.) and subsequent reflux under heating. By cooling the resulting solution under stirring down to around 60° C., isopropyl ether (30 ml) was dropwise added to the resulting solution, followed by further reflux under heating. By cooling the resulting solution under stirring down to around 60° C., seed crystal [crystal (V)] (15 mg) was added to the resulting solution. Then, the solution was cooled down to ambient temperature, followed by stirring at the same temperature for 2 hours. The deposited crystal was filtered off and washed with a mixture solution (1.5 ml) of isopropyl ether and tetrahydrofuran (10:1). The resulting crystal was dried in air at ambient temperature for about one week, to thereby recover the crystal (I) (1.44 g) of the depsipeptide derivative (IV).

EXAMPLE 3

Production of Crystal (I) (No.3)

The crystal (II) of the depsipeptide derivative (IV) was produced in the same manner as in Example 5 described below. Then, the crystal (1.5 g) was charged to a 50 ml three-necked flask, followed by addition of 3 ml of acetonitrile to dissolve the crystal at ambient temperature (25° C.) and subsequent reflux under heating. By cooling the resulting solution under stirring down to around 60° C., isopropyl ether (30 ml) was dropwise added to the resulting solution, followed by further reflux under heating. By cooling the resulting solution under stirring down to around 60° C., seed crystal [crystal (V)] (15 mg) was added to the resulting solution. Then, the solution was cooled down to ambient temperature, followed by stirring at the same temperature for 2 hours. The deposited crystal was filtered off and washed with a mixture solution (3 ml) of isopropyl ether and acetone (10:1). The resulting crystal was dried in air at ambient temperature for about one week, to thereby recover the crystal (I) (1.31 g) of the depsipeptide derivative (IV).

EXAMPLE 4

Production of crystal (I) (No.4)

The crystal (II) of the depsipeptide derivative (IV) was produced in the same manner as in Example 5 described below. Then, the crystal (1.5 g) was charged to a 50 ml three-necked flask, followed by addition of 3 ml of acetonitrile to dissolve the crystal at ambient temperature (26° C.) and subsequent reflux under heating. By cooling the resulting solution under stirring down to around 50° C., isopropyl ether (30 ml) was dropwise added to the resulting solution, followed by further reflux under heating. By cooling the resulting solution under stirring down to around 50° C., seed crystal [crystal (V)] (15 mg) was added to the resulting solution. Then, the solution was cooled down to ambient temperature, followed by stirring at the same temperature for 2 hours. The deposited crystal was filtered off and washed with a mixture solution (3 ml) of isopropyl ether and acetone (10:1). The resulting crystal was dried in air at ambient temperature for about one week, to thereby recover the crystal (I) (1.41 g) of the depsipeptide derivative (IV).

EXAMPLE 5

Production of Crystal (II)

The crystal (I) (15.0 g) of the depsipeptide derivative (IV) as recovered in Example 1 was charged to a 300 ml three-necked flask, followed by addition of 30 ml of ethanol to dissolve the crystal while refluxing under heating. After removing ethanol (15 ml) while refluxing under heating, the resulting solution was once cooled down to 50° C. Subsequently by adding isopropyl ether (300 ml) to the solution while gradually cooling the solution down to ambient temperature (25° C.), a crystal was deposited. By stirring further the solution at ambient temperature for one hour, the deposited crystal was filtered off and washed with isopropyl ether (5 ml). The resulting crystal was dried at 60° C. for 4 hours under reduced pressure and further dried in air at ambient temperature for one day, to recover the crystal (II) (12.0 g) of the depsipeptide derivative (IV).

EXAMPLE 6

Production of Crystal (III)

The crystal (II) (40 g) of the depsipeptide derivative (IV) recovered in the Example 5 above was charged to a one liter three-necked flask, followed by addition of 80 ml of ethyl acetate to subsequently heat the resulting mixture at 40° C. and dissolve the mixture therein under stirring. After subsequently refluxing the resulting solution under heating, the resulting solution was cooled down to 60° C., followed by addition of 200 ml of isopropyl ether to deposit a crystal. Subsequently, isopropyl ether (600 ml) was dropwise added to the resulting mixture over at 70° C. about 35 minutes, and thereafter, the mixture was stirred at the same temperature for 20 minutes. After cooling the mixture under stirring down to ambient temperature (27° C. ), the mixture was further stirred at the temperature (27° C.) for 4 hours, to filter off the deposited crystal. The resulting crystal was dried in air for about one week, whereby the crystal (III) (37.8 g) of the depsipeptide derivative (IV) was recovered.

Experimental Example 1

The crystals (I), (II) and (III) of the depsipeptide derivative (IV), thus recovered in the aforementioned manners, were examined about the filtration properties during crystallization, the specific volume and water content, by using the prior art crystal (V) for comparison.

The filtration properties during crystallization were evaluated on the following standards under observation with the naked eye.

⊚: very great filtration properties

◯: good filtration properties

Δ: poor filtration properties

X: very poor filtration properties

As to the specific volume, each crystal (5 g) was put in a 20 ml measuring cylinder, followed by tapping, and the value (ml/g) of a volume not any more decreased even after tapping was measured.

As to the water content, additionally, each crystal was left to stand at ambient temperature until its weight reached constant value, wherein an amount of water containing in the crystal was measured in %.

These results are collectively shown in Table 6.

TABLE 6

|  | Filtration property during crystallization | Specific volume (ml/g) | Water content (%) |
| --- | --- | --- | --- |
| Crystal (I) | × | 12.5/5.0 | 3.16 |
| Crystal (II) | ◎ | 8.2/5.0 | 0.98 |
| Crystal (III) | ○ | 16.2/5.0 | 0.20 |
| Prior art Crystal (V) | × | 16.0/5.0 | 2.45 |

The following were discussed on the basis of the Table. Herein the "good filtration properties during crystallization" and "small specific volume" herein function as indicators of production efficiency.

Firstly, the prior art crystal (V) has poor filtration properties during crystallization and a large specific volume, so the production efficiency thereof is markedly reduced in such manners that the number of the batches thereof during drying process is increased and that the drying time thereof is also prolonged and the like. Not shown in the Table, furthermore, the prior art crystal (V) has poor fluidity (large adhesion properties). Therefore, the crystal readily adheres to a conical drying machine during the course of discharge it from the machine, resulting in a prominent reduction of the yield because of such adhesion.

On the other hand, the crystal (II) of the present invention has great filtration properties during crystallization and a small specific volume, thereby resulting in the improvement of the production efficiency. In addition, as the crystal (II) has great fluidity, the crystal loss due to the adhesion to machines during the production process is reduced, resulting in increases the yield of the crystal.

Additionally, the crystal (I) of the present invention has such a small specific volume that the production efficiency can be improved.

Furthermore, the crystal (III) of the present invention has good filtration properties during crystallization, so the production efficiency thereof can be increased, compared with the prior art crystal (V).

INDUSTRIAL APPLICABILITY

Because the novel crystals (I), (II) and (III) of the depsipeptide derivative (IV) in accordance with the present invention are composed in above fashion, the yield of the crystals and production efficiency can be increased highly compared with the prior art crystal (V).

What is claimed is:

1. Crystal (I) of depsipeptide derivative (IV) represented by the following formula:

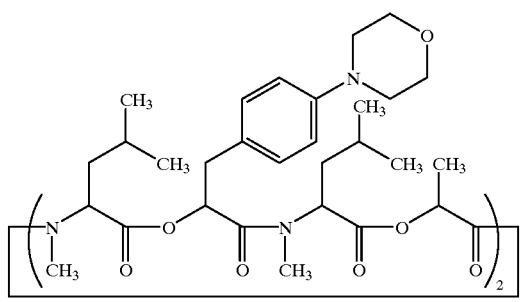

characterized in that the crystal (I) has an endothermic peak substantially at 155° C. by differential thermal analysis and substantially has the powdery X-ray diffraction characteristic properties described in Table 1:

TABLE 1

| 2θ value (°) | Relative Intensity (%) | 2θ value (°) | Relative Intensity (%) | 2θ value (°) | Relative Intensity (%) | 2θ value (°) | Relative Intensity (%) |
| --- | --- | --- | --- | --- | --- | --- | --- |
| 5.67 | 100.0 | 13.15 | 19.52 | 19.86 | 15.18 | 26.48 | 2.33 |
| 6.46 | 0.41 | 14.56 | 8.83 | 20.19 | 10.19 | 26.93 | 1.22 |
| 7.36 | 1.01 | 15.01 | 42.59 | 20.47 | 6.81 | 27.66 | 5.24 |
| 7.92 | 3.12 | 15.44 | 61.33 | 20.84 | 7.03 | 28.03 | 4.70 |
| 8.74 | 5.339 | 15.97 | 26.84 | 21.62 | 8.83 | 28.60 | 2.65 |
| 9.34 | 9.94 | 16.80 | 16.13 | 22.15 | 6.71 | 29.45 | 1.26 |
| 10.35 | 10.32 | 17.07 | 10.84 | 22.52 | 7.35 | 29.77 | 1.60 |
| 11.27 | 29.39 | 17.55 | 2.39 | 23.04 | 1.55 | 30.61 | 1.05 |
| 11.39 | 25.81 | 18.33 | 19.34 | 23.75 | 5.81 | 31.94 | 1.36 |
| 11.88 | 5.52 | 18.96 | 7.79 | 25.05 | 4.03 | | |
| 12.69 | 5.24 | 19.42 | 3.87 | 26.07 | 1.40. | | |

2. A method for producing crystal (I) of depsipeptide derivative represented by formula (IV):

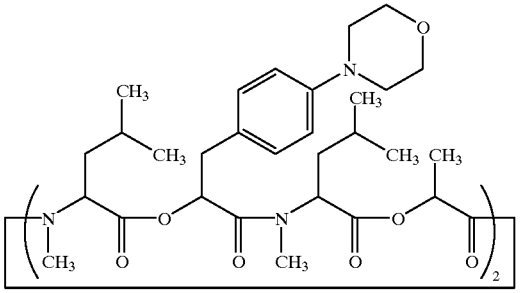

comprising:

(1) dissolving depsipeptide derivative (IV) in acetone and adding water to the resulting mixture for crystallization, or (2) dissolving depsipeptide derivative (IV) in tetrahydrofuran, acetonitrile or acetone and adding isopropyl ether to the resulting mixture for crystallization.

3. Crystal (II) of depsipeptide derivative represented by formula (IV)

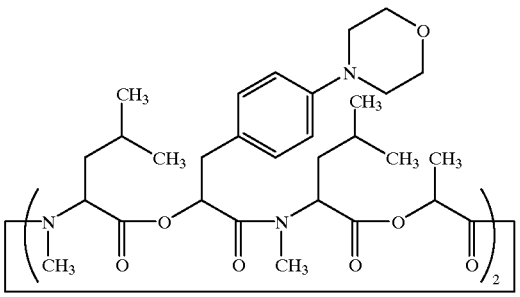

characterized in that the crystal (II) has an endothermic peak substantially at 182° C. by differential thermal analysis and substantially has the powdery X-ray diffraction characteristic properties described in Table 2:

TABLE 2

| 2 θ value (°) | Relative intensity (%) | 2 θ value (°) | Relative intensity (%) | 2 θ value (°) | Relative intensity (%) | 2 θ value (°) | Relative intensity (%) |
|---|---|---|---|---|---|---|---|
| 4.79 | 35.86 | 13.56 | 47.83 | 19.10 | 47.83 | 25.00 | 6.48 |
| 4.89 | 35.50 | 14.20 | 32.70 | 19.51 | 32.02 | 25.36 | 6.63 |
| 5.58 | 14.69 | 14.64 | 30.02 | 19.91 | 17.57 | 26.06 | 4.65 |
| 7.00 | 1.16 | 15.75 | 41.82 | 21.39 | 23.82 | 27.31 | 8.61 |
| 9.09 | 8.79 | 15.56 | 52.50 | 22.02 | 13.34 | 27.95 | 8.61 |
| 9.69 | 5.45 | 16.26 | 66.32 | 22.54 | 14.01 | 29.06 | 6.48 |
| 10.52 | 100.0 | 16.63 | 40.67 | 22.84 | 16.58 | 29.60 | 3.12 |
| 10.85 | 31.10 | 17.07 | 40.29 | 23.16 | 17.32 | 30.38 | 3.79 |
| 11.49 | 7.10 | 18.34 | 32.70 | 23.82 | 26.21 | 31.75 | 2.07 |
| 12.40 | 11.86 | 18.73 | 24.40 | 24.44 | 9.51 | | |

4. A method for producing crystal (II) of the depsipeptide derivative represented by formula (IV):

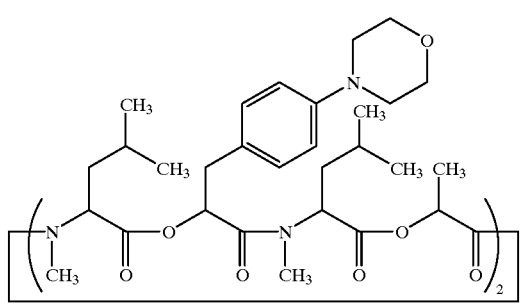

comprising:

dissolving crystal (I) of the depsipeptide derivative (IV) in ethanol and adding isopropyl ether to the resulting mixture for crystallization.

5. Crystal (III) of depsipeptide derivative (IV):

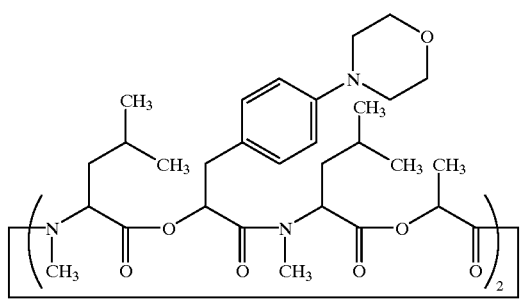

characterized in that the crystal (III) has an endothermic peak substantially at 194° C. by differential thermal analysis and substantially has the powdery X-ray diffraction characteristic properties described in Table 3:

TABLE 3

| 2 θ value (°) | Relative intensity (%) | 2 θ value (°) | Relative intensity (%) | 2 θ value (°) | Relative intensity (%) | 2 θ value (°) | Relative intensity (%) |
|---|---|---|---|---|---|---|---|
| 6.02 | 100.0 | 12.17 | 30.53 | 19.04 | 14.75 | 26.07 | 3.83 |
| 6.20 | 87.04 | 13.20 | 5.81 | 19.44 | 7.78 | 26.73 | 2.78 |
| 6.30 | 50.17 | 14.45 | 16.17 | 19.98 | 10.99 | 28.19 | 2.66 |
| 6.82 | 2.60 | 15.19 | 19.22 | 21.21 | 11.72 | 29.13 | 1.61 |

TABLE 3-continued

| 2 θ value (°) | Relative intensity (%) | 2 θ value (°) | Relative intensity (%) | 2 θ value (°) | Relative intensity (%) | 2 θ value (°) | Relative intensity (%) |
|---|---|---|---|---|---|---|---|
| 8.08 | 1.22 | 16.10 | 19.22 | 21.99 | 17.36 | 30.05 | 1.22 |
| 9.45 | 2.32 | 16.70 | 26.47 | 22.16 | 11.97 | 30.61 | 1.26 |
| 9.64 | 1.90 | 16.87 | 24.10 | 22.88 | 8.40 | 31.27 | 0.76 |
| 10.48 | 2.10 | 17.74 | 6.62 | 22.99 | 9.94 | | |
| 12.03 | 20.51 | 18.45 | 7.38 | 24.26 | 10.52 | | |

6. A method for producing crystal (III) of the depsipeptide derivative (IV):

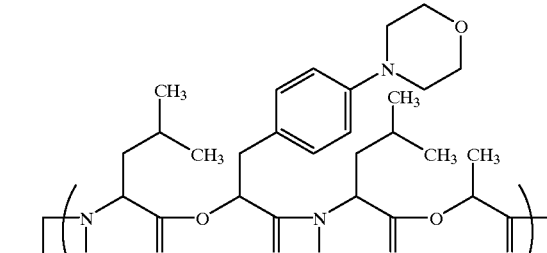

comprising:

dissolving crystal (II) of the depsipeptide derivative (IV) in ethyl acetate and adding isopropyl ether to the resulting mixture for crystallization.

7. A crystal of a depsipeptide derivative represented by formula (IV):

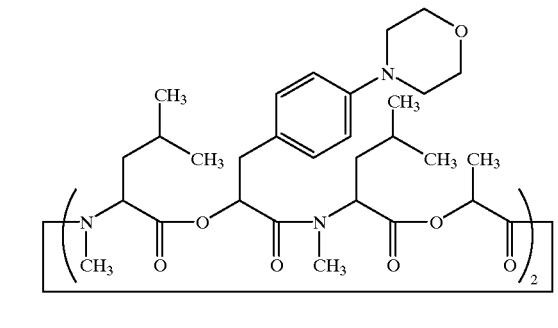

having an endothermic peak substantially at 155° C. as determined by differential thermal analysis and which is produced by a method comprising:

(1) dissolving depsipeptide derivative (IV) in acetone and adding water to the resulting mixture for crystallization, or (2) dissolving depsipeptide derivative (IV) in tetrahydrofuran, acetonitrile or acetone and adding isopropyl ether to the resulting mixture for crystallization.

8. An antiparasitic composition comprising the crystal of claim 7.

9. A crystal of a depsipeptide derivative represented by formula (IV):

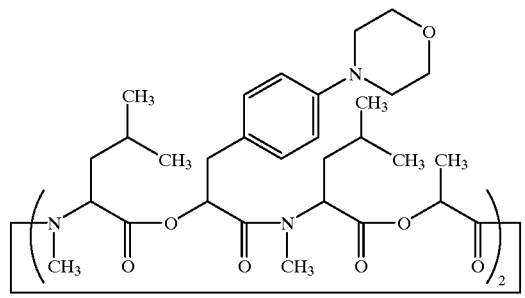

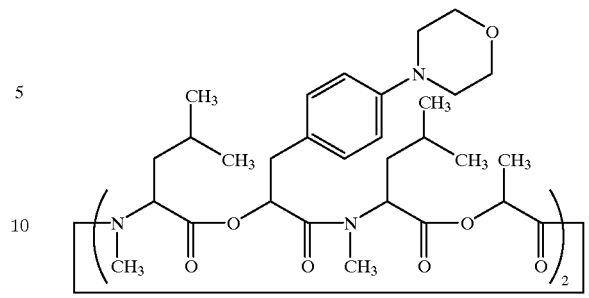

having an endothermic peak substantially at 182° C. as determined by differential thermal analysis.

10. An antiparasitic composition comprising the crystal of claim 9.

11. A crystal of a depsipeptide derivative represented by formula (IV):

having an endothermic peak substantially at 194° C. as determined by differential thermal analysis.

12. An antiparasitic composition comprising the crystal of claim 11.

* * * * *